US00PP21221P2

(12) United States Plant Patent
Zaias-Fast

(10) Patent No.: US PP21,221 P2
(45) Date of Patent: Aug. 24, 2010

(54) *MUSA* PLANT NAMED 'CHEEKA'
(50) Latin Name: *Musa acuminata*
Varietal Denomination: Cheeka

(76) Inventor: Magaly Zaias-Fast, 11068 NW. 3rd St., Coral Springs, FL (US) 33071

( * ) Notice: Subject to any disclaimer, the term of this patent is extended or adjusted under 35 U.S.C. 154(b) by 0 days.

(21) Appl. No.: 12/380,499

(22) Filed: Feb. 27, 2009

(51) Int. Cl.
*A01H 5/00* (2006.01)

(52) U.S. Cl. ..... Plt./156

(58) Field of Classification Search ..... Plt./156, Plt./160
See application file for complete search history.

*Primary Examiner*—Susan B McCormick Ewoldt

(57) ABSTRACT

A new and distinct *Musa acuminata* cultivar named 'Cheeka' is disclosed, characterized a very compact plant with predominately solid green foliage and strong foliage resistant to tearing and breakage. The new cultivar is a *Musa acuminata* suitable as an indoor pot plant.

1 Drawing Sheet

Figure 1:
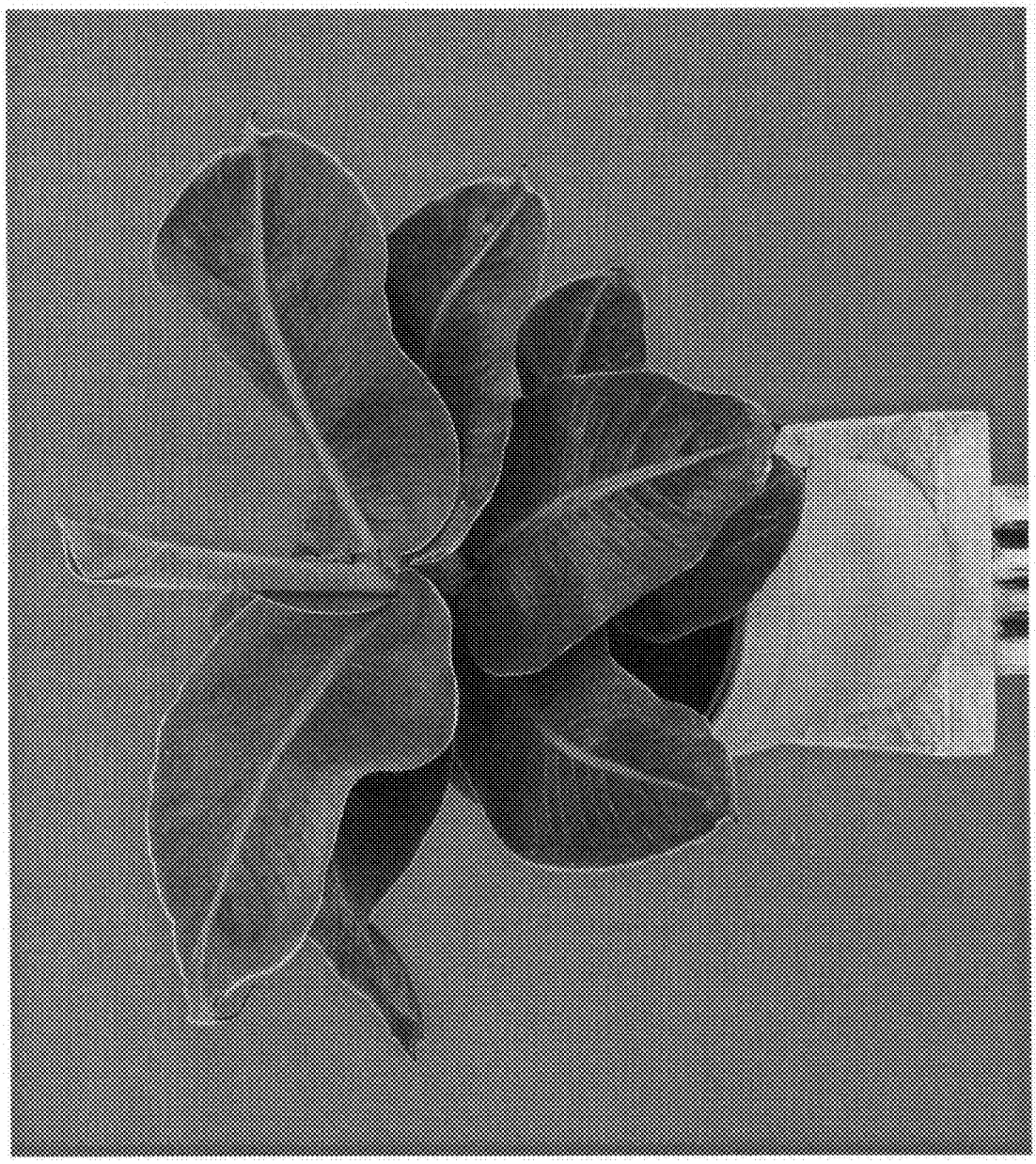

Latin name of the genus and species: *Musa acuminata.*
Variety denomination: 'Cheeka'.

BACKGROUND OF THE INVENTION

The new cultivar is a chance, whole plant mutation selected by the inventor, Magaly Zais-Fast, a citizen of the United States, in 1995 at a commercial greenhouse located near Bangkok, Thailand. 'Cheeka' was found as a single, whole plant mutation growing in a commercial planting of the parent variety *Musa acuminata* 'Kluai Khai'.

Asexual reproduction of the new cultivar 'Cheeka' was first performed by tissue culture at a commercial laboratory in Thailand 2001. 'Cheeka' has been reproduced by micropropagation and has shown that the unique features of this cultivar are stable and reproduced true to type.

SUMMARY OF THE INVENTION

The cultivar 'Cheeka' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Cheeka.' These characteristics in combination distinguish 'Cheeka' as a new and distinct *Musa* cultivar:

1. Very compact plant habit.
2. Predominately solid green foliage.
3. Suitability as an indoor pot plant.
4. Strong foliage resistant to tearing and breakage.

PARENT COMPARISON

Plants of the new cultivar 'Cheeka' are similar to plants of the unpatented parent variety, *Musa acuminata* 'Kluai Khai' in most horticultural characteristics, however, plants of 'Cheeka' are much shorter and more compact than the parent variety. Additionally the central stem of 'Cheeka' is white when immature, purple/red at maturity, whereas the central stem of 'Kluai Khai' is yellow green, with brown or black blotching.

COMMERCIAL COMPARISON

'Cheeka' can be compared to the patented commercial variety *Musa* 'Little Prince' U.S. Plant Pat. No. 15,255. Plants of 'Little Prince' are similar to plants of 'Cheeka' in most horticultural characteristics, however, 'Cheeka' is more compact, with foliage that is more resistant to tearing, and with less foliage color variegation.

BRIEF DESCRIPTION OF THE PHOTOGRAPH

The accompanying photograph in FIG. 1 illustrates in full color a typical plant of 'Cheeka' grown in a greenhouse. This plant is approximately 18 months old, shown in a 15 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Cheeka' plants grown in a climate controlled greenhouse in Evergem, the Netherlands. Temperatures ranged from 18° C. to 22° C. at night to 18° C. to 22° C. during the day. No artificial light, photoperiodic treatments or chemical treatments were given to the plants. Measurements and numerical values represent averages of typical plant types.
Botanical classification: *Musa acuminata* cultivar 'Cheeka'.

PLANT

Growth habit: Tender perennial with a single pseudostem.
Height: Approximately 26.3 cm.
Plant spread: Approximately 34.6 cm in a 15 cm pot.
Normal pot size: 13, 15, 18 cm.
Growth Rate: Moderate to slow.
Branching characteristics: Upright, non-branching.
Number of leaves per stem: Approximately 17.
Age of plant described: Approximately 18 months.
Psuedostem length: Average 10.8 cm.

Psuedostem width: Average 1.7 cm.
Psuedostem appearance: Smooth, Slightly glossy.
Psuedostem strength: Very strong.
Psuedostem color:
*Immature.*—Near RHS White N155C.
*Mature.*—Near RHS Greyed-Purple 183B.

FOLIAGE

Leaf:
*Arrangement.*—Whorled, single.
*Average length.*—Approximately 119.3 cm.
*Average width.*—Approximately 12.6 cm.
*Internode length.*—0.3 cm.
*Shape of blade.*—Ovate.
*Aspect.*—Slightly undulating, very slightly recurved towards tip on older leaves.
*Apex.*—Abruptly acute.
*Base.*—Cordate.
*Margin.*—Entire.
*Texture of top surface.*—Smooth, moderately glossy.
*Texture of bottom surface.*—Smooth, moderately glossy.
*Color.*—Young foliage upper side: Near RHS Green 141B. Young foliage under side: Near RHS Green 146A, Waxy sheen over entire leaf near Greyed-Green 198B. Mature foliage upper side: Near RHS Green 141A. Mature foliage under side: Near RHS Green 137A.
*Venation.*—Type: Pinnately parallel. Venation coloration: Upperside: Near RHS Green; 143B. Underside: Near RHS Yellow-Green 144C.
*Other foliage characteristics.*—Strong foliage resists tearing and breakage during transport and other potential mechanical damage.

Petiole:
*Length.*—Average 5.4 cm.
*Diameter.*—Average 3.9 cm.
*Coloration.*—Outer: Lower part near RHS Greyed-purple 183B, upper part (closer to the leaf blade) yellow-green 144C. Inner: Near RHS Yellow-green 145D, greener towards the leaf blade, near 144C.

INFLORESCENCE

Flowers not observed in this cultivar.

OTHER CHARACTERISTICS

Disease resistance: Neither resistance nor susceptibility to diseases or pests has been observed in this variety.
Drought tolerance and cold tolerance: Observed to tolerate temperatures to 40° C. without any negative effects. Temperature tolerance above this range has not been observed. Tolerance of cold temperatures has not been observed, as the variety has been only tested as an indoor ornamental potted plant.
Fruit/seed production: Not observed.

What is claimed is:

1. A new and distinct cultivar of *Musa acuminata* plant named 'Cheeka' as herein illustrated and described.

* * * * *